(12) United States Patent
Gerardi et al.

(10) Patent No.: US 9,175,052 B2
(45) Date of Patent: Nov. 3, 2015

(54) TOBACCO-DERIVED PROTEIN COMPOSITIONS

(71) Applicant: R.J. Reynolds Tobacco Company, Winston-Salem, NC (US)

(72) Inventors: Anthony Richard Gerardi, Winston-Salem, NC (US); Crystal Dawn Hege Byrd, Lexington, NC (US); Thaddeus Jude Jackson, High Point, NC (US); Chelsea Allison Betts, Winston-Salem, NC (US); John-Paul Mua, Advance, NC (US); Kyle Ford, Germanton, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 0 days.

(21) Appl. No.: 13/896,656

(22) Filed: May 17, 2013

(65) Prior Publication Data

US 2014/0343254 A1 Nov. 20, 2014

(51) Int. Cl.
| | |
|---|---|
| *C07K 1/34* | (2006.01) |
| *C07K 14/415* | (2006.01) |
| *A23J 3/14* | (2006.01) |
| *A23K 1/16* | (2006.01) |
| *A23L 1/305* | (2006.01) |
| *A23L 2/66* | (2006.01) |
| *A24B 15/18* | (2006.01) |
| *A24B 15/24* | (2006.01) |
| *A23J 1/00* | (2006.01) |
| *A23L 1/015* | (2006.01) |

(52) U.S. Cl.
CPC ............ *C07K 14/415* (2013.01); *A23J 1/007* (2013.01); *A23J 3/14* (2013.01); *A23K 1/1631* (2013.01); *A23L 1/0152* (2013.01); *A23L 1/0156* (2013.01); *A23L 1/3055* (2013.01); *A23L 2/66* (2013.01); *A24B 15/18* (2013.01); *A24B 15/24* (2013.01); *C12Y 401/01039* (2013.01)

(58) Field of Classification Search
None
See application file for complete search history.

(56) References Cited

U.S. PATENT DOCUMENTS

| | | |
|---|---|---|
| 3,684,520 A | 8/1972 | Bickoff et al. |
| 3,823,128 A | 7/1974 | Bickoff et al. |
| 3,959,246 A | 5/1976 | Bickoff et al. |
| 4,268,632 A | 5/1981 | Wildman et al. |
| 4,289,147 A | 9/1981 | Wildman et al. |
| 4,333,871 A | 6/1982 | De Jong |
| 4,340,676 A | 7/1982 | Bourque |
| 4,347,324 A | 8/1982 | Wildman et al. |
| 4,400,471 A | 8/1983 | Johal |
| 4,493,854 A | 1/1985 | Friedrich et al. |
| 4,588,691 A | 5/1986 | Johal |
| 4,675,198 A | 6/1987 | Sevenants |
| 4,941,484 A | 7/1990 | Clapp et al. |
| 6,033,895 A * | 3/2000 | Garger et al. ............. 435/239 |
| 7,048,211 B2 | 5/2006 | Bratcher et al. |
| 7,337,782 B2 | 3/2008 | Thompson |
| 7,638,155 B2 | 12/2009 | Irwin et al. |
| 2008/0178894 A1 | 7/2008 | Zimmermann |
| 2010/0093054 A1 | 4/2010 | Lo et al. |
| 2012/0141648 A1 | 6/2012 | Morton et al. |
| 2013/0072661 A1 | 3/2013 | Kale |
| 2014/0271952 A1 | 9/2014 | Mua et al. |

FOREIGN PATENT DOCUMENTS

| | | |
|---|---|---|
| EP | 1 067 946 | 1/2001 |
| EP | 1 691 759 | 8/2006 |
| EP | 2 403 888 | 1/2012 |
| WO | WO 2008/143914 | 11/2008 |
| WO | WO 2011/078671 | 6/2011 |

OTHER PUBLICATIONS

Frega et al. "Chemical Composition of Tobacco Seeds (*Nicotiana tabacum* L.)" JAOCS 1991 68 29-33.*
PubChem http://pubchem.ncbi.nlm.nih.gov//compound/89594?from=summary#section=Safety-and-Hazards.*
Fischer et al., "Optimization of Nicotine Extraction from Tobacco Using Supercritical Fluid Technology with Dynamic Extraction Modeling," *J. Agric. Food Chem.*, 1996, pp. 1258-1264, vol. 44.
Krishnan et al., "A Rapid Method for Depletion of Rubisco From Soybean (Glycine Max) Leaf for Proteomic Analysis of Lower Abundance Proteins," *Phytochemistry*, 2009, pp. 1958-1964, vol. 70.
Lamsen et al., "Impacts of Supercritical Extraction on GC/MS Profiles of Volatiles in Whey Protein Isolate Sampled by Solid-Phase Microextraction," *Journal of Food Processing and Preservation*, 2011, pp. 869-883, vol. 35.
Siceloff, "A Revolutionary Upheaval? Tobacco for Protein" *N.C. Insight*, Jun. 1981, pp. 28-32. http://www.nccppr.org/drupal/content/insightarticle/918/tobacco-for-protein.
Maheshwari et al., "Off-Flavor Removal from Soy-Protein Isolate by Using Liquid and Supercritical Carbon Dioxide," *Journal of the American Oil Chemist Society*, 1995, pp. 1107-1115, vol. 72, No. 10.

\* cited by examiner

*Primary Examiner* — David J Steadman
*Assistant Examiner* — Paul Holland
(74) *Attorney, Agent, or Firm* — Womble Carlyle Sandridge & Rice, LLP

(57) ABSTRACT

The disclosure describes methods for the purification of protein-enriched extracts to provide concentrates and isolates and methods for incorporation of such materials into products. The purification methods are adapted for removal of one or more of ash, metal salts, alkaloids, particulates, heavy metals, and other impurities and/or contaminants from extracts, as well as modifying the sensory characteristics (e.g., odor, color, and/or taste characteristics) of extracts. The methods generally include diafiltration, treatment with functionalized resins, and supercritical extraction. A protein composition in the form of a concentrate or isolate is provided, the protein composition including RuBisCO, F2 fraction proteins, or combination thereof extracted from a plant of the *Nicotiana* species, wherein the protein composition is characterized by one or more of: an ash content of less than about 15% by weight; a nicotine content of less than about 10 µg/g; and a heavy metal content of less than about 60 µg/g.

22 Claims, 2 Drawing Sheets

TOBACCO-DERIVED PROTEIN COMPOSITIONS

FIELD OF THE INVENTION

The present invention relates primarily to products made or derived from tobacco, or that otherwise incorporate tobacco or components of tobacco, and are intended for human consumption. Of particular interest are ingredients or components obtained or derived from plants or portions of plants from the *Nicotiana* species.

BACKGROUND OF THE INVENTION

Many uses of tobacco have been proposed. For example, tobacco has been smoked in pipes, and tobacco has been used for smoking in cigarettes and cigars. See, for example, *Tobacco Production, Chemistry and Technology*, Davis et al. (Eds.) p. 346 (1999). In recent years, there have been proposed various ways of providing many of the sensations of smoking, but without delivering considerable quantities of incomplete combustion and pyrolysis products that result from burning tobacco. See, for example, the background art set forth in U.S. Pat. No. 7,503,330 to Borschke et al. and U.S. Pat. No. 7,726,320 to Robinson et al., and U.S. patent application Ser. No. 13/840,264 to Novak, III et al., filed Mar. 15, 2013 and Ser. No. 13/647,670 to Gerardi, filed Oct. 9, 2012. Tobacco also has been enjoyed in so-called smokeless forms. See, for example, the background art set forth in US Pat. Pub. 2012/0272976 to Byrd et al. In addition, various materials derived from tobacco have been proposed to have uses in certain industrial applications. See, for example, U.S. Pat. No. 2,098,836 to Ressler; U.S. Pat. No. 2,232,662 to Hockenyos; U.S. Pat. No. 4,347,324 to Wildman et al. and U.S. Pat. No. 4,289,147 to Wildman et al., and US Pat. Pub. Nos. 2011/01287681 to DeVall and 2012/0260929 to Coleman et al.

Methods of extracting proteins from tobacco and tobacco components have been proposed in U.S. patent application Ser. No. 13/830,063 to Mua et al., filed Mar. 14, 2013. It would be desirable to provide a purified, tobacco-derived protein composition for use in tobacco formulations useful in the manufacture of smoking articles and/or smokeless tobacco products, as well as for incorporation into other products such as nutritional supplements.

SUMMARY OF THE INVENTION

The present invention provides materials derived from plants, particularly from plants of the *Nicotiana* species. In preferred embodiments, the materials are provided in what can be considered to be a purified form. The invention also provides methods for extracting components from plants, e.g., *Nicotiana* species, and methods for processing those components. In particular, the invention provides protein concentrates, isolates, and other forms of products derived from tobacco materials, methods for obtaining such protein concentrates, isolates, and other forms of products, and methods for incorporation of such protein concentrates, isolates, and other forms of products into various types of compositions.

In one aspect of the invention is provided a method for reducing the content of undesirable components in a protein-enriched material, the method comprising: a) providing a plant-derived, protein-enriched material comprising RuBisCO, F2 fraction proteins, or a combination thereof (e.g., in an amount of at least about 40% by weight), wherein the plant-derived, protein-enriched material further comprises undesirable components; b) dissolving at least a portion of the plant-derived, protein-enriched material in a solvent to form a solution; and c) subjecting the plant-derived, protein-enriched material solution to diafiltration by passing the solution through one or more ultrafiltration membranes to afford a retentate comprising a protein concentrate or isolate having a reduced amount of undesirable components as compared with the plant-derived, protein-enriched material. In preferred embodiments, the undesirable components comprise ash, metals, particulate solids, alkaloids (e.g., nicotine), and the like.

With regard to the foregoing method, the specific parameters of the diafiltration can vary. For example, the solvent in some embodiments can comprise a liquid having an aqueous character (e.g., water, including purified water, deionized water, tap water, etc.). In some embodiments, the solvent is basic (having a pH greater than 7). The plant-derived, protein-enriched material can vary and in certain embodiments, comprises material from a plant of the *Nicotiana* species. The ultrafiltration membrane can, in some embodiments, have a molecular weight cutoff of between about 1 kDa and about 150 kDa. For example, the ultrafiltration membrane can have a molecular weight cutoff of about 5 kDa.

Following such a method, the protein concentrate or isolate may, in some embodiments, have an ash content that is reduced at least about 25% as compared with the plant-derived, protein-enriched material. In certain embodiments, the protein concentrate or isolate has an ash content of less than about 10% by weight. Following such a method, the protein concentrate or isolate may, in some embodiments, have a nicotine content of less than about 5 μg/g. In certain embodiments, the protein concentrate or isolate has a nicotine content of less than about 1 μg/g.

In another aspect of the invention is provided a method for reducing the content of undesirable components in a protein-enriched material, the method comprising: a) providing a plant-derived, protein-enriched material comprising RuBisCO, F2 fraction proteins, or a combination thereof (e.g., in an amount of at least about 40% by weight), wherein the plant-derived, protein-enriched material further comprises undesirable components; b) dissolving at least a portion of the plant-derived, protein-enriched material in a solvent to form a solution; c) contacting the plant-derived, protein-enriched material solution with a functionalized resin to afford a treated solution comprising a protein concentrate or isolate having a reduced amount of content of undesirable components; and d) separating the treated solution from the functionalized resin. In preferred embodiments of the foregoing method, the undesirable components are heavy metals such as copper, cadmium, lead, nickel, and combinations thereof.

With regard to the foregoing method, the specific parameters of the contacting step can vary. For example, the solvent in some embodiments can comprise a liquid having an aqueous character (e.g., water, including purified water, deionized water, tap water, etc.). In some embodiments, the solvent is basic (having a pH greater than 7). The plant-derived, protein-enriched material can vary and in certain embodiments, comprises material from a plant of the *Nicotiana* species. In certain embodiments, the contacting step comprises stirring the plant-derived, protein-enriched material solution with the functionalized resin. In other embodiments, the contacting step comprises passing the plant-derived, protein-enriched material solution through a column comprising the functionalized resin.

The makeup of the functionalized resin can vary. For example, the functionalized resin can comprise a resin functionalized with triaminetetraacetic acid groups or salts thereof (e.g., triaminetetraacetate sodium salt groups). The contacting step can optionally be conducted at an elevated temperature (e.g., between about room temperature and about 80° C.). the contacting step can optionally comprise agitating the plant-derived, protein-enriched material solution and the functionalized resin (e.g., by stirring, shaking, or a combination thereof).

Following such a method, the protein concentrate or isolate can, in some embodiments, have an amount of one or more of copper, cadmium, lead, and nickel that is reduced at least about 25% as compared with the plant-derived, protein-enriched material. In certain embodiments, the protein concentrate or isolate has an amount of one or more of copper, cadmium, lead, and nickel that is reduced at least about 50% as compared with the plant-derived, protein-enriched material.

In a further aspect of the invention is provided a method for modifying the sensory characteristics (e.g., odor and/or taste characteristics) in a protein-enriched material, the method comprising: a) providing a plant-derived, protein-enriched material comprising RuBisCO, F2 fraction proteins, or a combination thereof (e.g., in an amount of at least about 40% by weight), wherein the plant-derived, protein-enriched material further exhibits an initial odor or taste; b) extracting components from the protein-enriched extract with a solvent while the solvent is in a supercritical state to provide a protein concentrate or isolate having an altered odor and/or taste; and c) separating the protein concentrate or isolate from the unextracted residue. In some preferred embodiments, the modification of sensory characteristics comprises a reduction in odor. In some preferred embodiments, the modification of sensory characteristics comprises a modification of the taste characteristics.

With regard to the foregoing method, the plant-derived, protein-enriched material subjected to supercritical extraction can be, for example, provided in spray dried or freeze-dried form. The method can optionally further comprise moistening the plant-derived, protein-enriched material prior to the extracting step with water to provide a plant-derived, protein-enriched material having between about 1% and about 50% moisture by weight. The extraction solvent can, in some embodiments, comprise supercritical carbon dioxide. The solvent can optionally comprise a modifier in an amount of up to about 30% by volume. Exemplary modifiers include, but are not limited to, the group consisting of ethanol, 1-butanol, isopropanol, methanol, 1-propanol, and mixtures thereof.

In certain embodiments, following treatment, the protein concentrate or isolate is characterized by a decrease in salty flavor as compared with the plant-derived, protein-enriched material. In some embodiments, the protein concentrate or isolate is characterized by a decrease in nicotine as compared with the plant-derived, protein-enriched material. For example, in some embodiments, the method can provide a reduction in nicotine of at least about 80%.

In a still further aspect of the invention is provided a method for reducing the content of undesirable components and/or modifying the sensory characteristics of a protein-enriched material, the method comprising providing a plant-derived, protein-enriched material comprising RuBisCO, F2 fraction proteins, or a combination thereof (e.g., in an amount of at least about 40% by dry weight), wherein the plant-derived, protein-enriched material further comprises one or more undesirable characteristics or impurities selected from the group consisting of ash, nicotine, heavy metals, odor, taste, or a combination thereof; and one or more of the following steps: a) dissolving at least a portion of the plant-derived, protein-enriched material in a solvent to form a solution and subjecting the plant-derived, protein-enriched material solution to diafiltration by passing the solution through one or more ultrafiltration membranes to afford a retentate comprising a protein concentrate or isolate having a reduced amount of ash, nicotine, or a combination thereof as compared with the plant-derived, protein-enriched material; b) dissolving at least a portion of the plant-derived, protein-enriched material in a solvent to form a solution, contacting the plant-derived, protein-enriched material solution with a functionalized resin to afford a treated solution comprising a protein concentrate or isolate having a reduced amount of one or more of copper, cadmium, lead, and nickel, and separating the treated solution from the functionalized resin; and c) extracting components from the protein-enriched extract with a solvent while the solvent is in a supercritical state to provide a protein concentrate or isolate having altered odor, taste, or a combination thereof, and separating the protein concentrate or isolate from the unextracted residue.

Also provided according to the present disclosure are protein concentrates or isolates obtained according to any of the methods described herein. Other aspects of the invention provide a dietary supplement, food, beverage, personal care item, pharmaceutical product, or pet food comprising the protein concentrates or isolates provided according to such methods.

In one aspect, the invention provides a protein composition in the form of a protein concentrate or isolate comprising RuBisCO, F2 fraction proteins, or a combination thereof extracted from a plant of the *Nicotiana* species, wherein the protein concentrate or isolate is characterized by one or more of the following: a) an ash content of less than about 15% by weight on a dry weight basis (e.g., less than about 10% by weight on a dry weight basis); b) a nicotine content of less than about 10 µg/g (e.g., less than about 5 µg/g); and c) a heavy metal content of less than about 60 µg/g (e.g., less than about 50 µg/g or less than about 40 µg/g).

In certain embodiments, the dry weight of RuBisCO, F2 fraction proteins, or a combination thereof in the protein compositions of the invention is at least about 70%, at least about 80%, or at least about 90%. In certain embodiments, the combined concentration of cadmium, copper, lead, and nickel in the protein compositions of the invention is less than about 40 µg/g or less than about 20 µg/g. Advantageously, the protein composition of the invention is odorless.

In yet another aspect, the invention provides dietary supplements, foods, beverages, personal care items, pharmaceutical products, or pet foods comprising the protein composition described herein or made by the processes described herein.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE PREFERRED EMBODIMENTS

Figure 1:
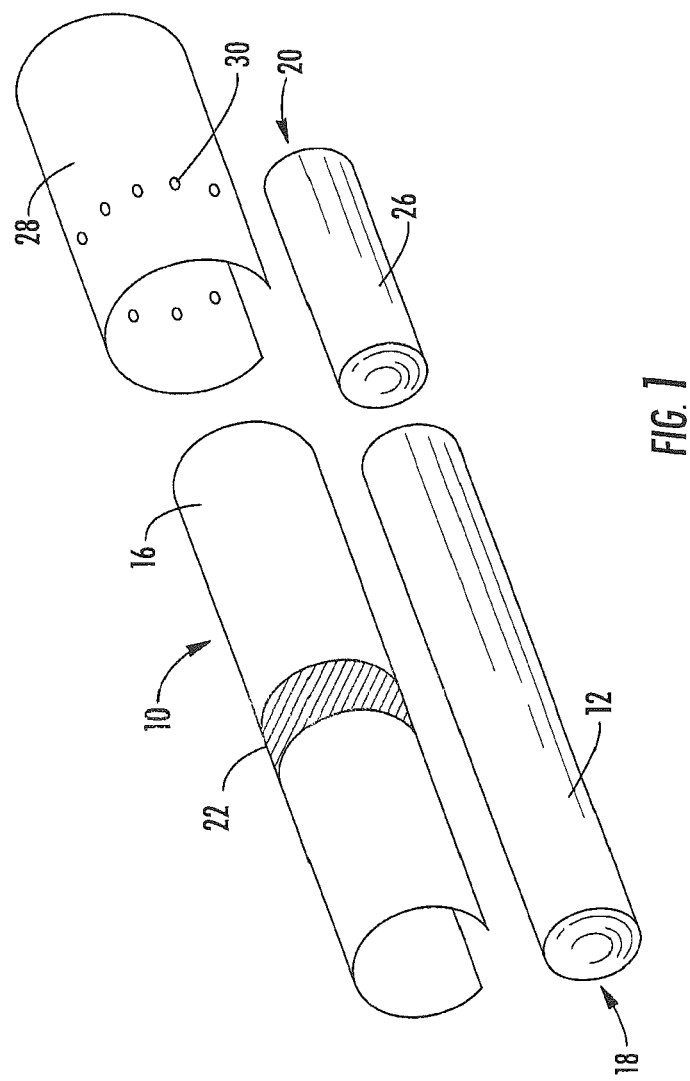
FIG. 1 is an exploded perspective view of a smoking article having the form of a cigarette, showing the smokable material, the wrapping material components, and the filter element of the cigarette.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

Generally, the present invention provides methods for purifying biomass-derived protein extracts. In one preferred embodiment, the biomass-derived protein extract comprises protein derived from a plant of the *Nicotiana* species. Often, methods of deriving protein from various biomasses results in a protein-enriched material that is not pure protein and may contain various other components extracted from the biomass. For example, in certain embodiments the crude protein-enriched material extracted from the biomass can further comprise such substances as lipids, chlorophyll, tannins, minerals, plant structural components, and phenolic pigments.

Although the present disclosure focuses primarily on proteins extracted from tobacco, it is noted that the methods may be generally applicable to crude protein materials extracted from plant materials other than tobacco. The methods described herein are thus intended to be applicable to any plant comprising green leaves and/or any plant believed to comprise proteins. In some embodiments, the methods are applicable to trees, bushes, grasses, ferns, vines, mosses, algae, and herbs. For example, the methods for preparing and purifying a protein-enriched material according to the present disclosure are in some embodiments applicable to such plants as spinach, alfalfa, Swiss chard, kale, chicory, amaranth, barley leaves, mustard greens, clover, carrot leaves, and beet leaves.

According to the present disclosure, a protein-enriched material can be further processed to provide a purer protein composition, such as a composition in the form of a concentrate or isolate. By "protein-enriched material" is meant a material (e.g., an extract) that has been derived from a plant and which contains one or more types of protein. The crude protein-enriched materials described herein generally comprise an amount of undesirable components/impurities such as ash, metal salts, trace metals, alkaloids (e.g., nicotine), precipitates, and other residual materials. Further, the protein-enriched materials may exhibit undesirable sensory or organoleptic characteristics (e.g., taste characteristics, odor, and/or color). By "protein concentrate" as used herein is meant a material comprising between about 29% and about 89% by weight protein on a dry weight basis. By "protein isolate" as used herein is meant a material comprising about 90% or more protein by weight on a dry weight basis.

Advantageously according to the invention, methods are provided for purifying protein-enriched materials to provide concentrates and/or isolates containing minimal amounts of certain undesirable components/impurities. For example, in certain embodiments, protein-enriched materials are processed to remove an amount of one or more of ash, metal salts, trace metals, heavy metals, alkaloids, and/or other impurities present and to thus increase the protein content of the material, giving a protein concentrate or a protein isolate of greater purity. In certain embodiments, protein-enriched materials are processed to modify sensory characteristics, e.g., by removing odor and/or color and/or by modifying the taste characteristics. Accordingly, the invention also provides protein compositions comprising minimal amounts (e.g., less than about 10% by weight, less than about 5% by weight, less than about 4% by weight, less than about 3% by weight, less than about 2% by weight, less than about 1% by weight, less than about 0.5% by weight, less than about 1% by weight, less than about 0.1% by weight, less than about 0.01% by weight, or undetectable amounts) of such undesirable components/impurities on a dry weight basis.

The present disclosure is applicable, in some embodiments, for large scale production, where the term large scale production refers to processing large quantities of a biomass on a mass production level. The team "biomass" and related terms such as "biomatter" and "plant source" are understood to refer to any portion of a harvested plant that may be processed to extract, separate, or isolate components of interest therefrom. The processing may be carried out in relation to various plants or portions thereof, such as seeds, flowers, stalks, stems, roots, tubers, leaves, or any further portions of the plant.

In particular embodiments, the methods described herein can be particularly relevant to the isolation and/or purification of a crude protein-containing material (e.g., extract) obtained from a tobacco plant material or a portion thereof. Exemplary tobacco plant materials used in accordance with the present disclosure may be of some form of a plant of the *Nicotiana* species, as described for example, in US Pat. Publ. No. 2012/0272976 to Byrd et al., which is incorporated by reference herein. Further descriptions of various types of tobaccos, growing practices and harvesting practices are set forth in *Tobacco Production, Chemistry and Technology*, Davis et al. (Eds.) (1999), which is incorporated herein by reference. Additional information on types of *Nicotiana* species suitable for use in the present invention can be found in US Pat. Appl. Pub. No. 2012/0192880 to Dube et al., which is incorporated by reference herein. The plant material may comprise material derived from an entire plant or any portion of a plant of the *Nicotiana* species. See, for example, the portions of tobacco plants set forth in US Pat. Appl. Pub. Nos. 2011/0174323 to Coleman, III et al. and 2012/0192880 to Dube et al., which are incorporated by reference herein.

The plant of the *Nicotiana* species can be employed in either an immature or mature form, and can be used in either a green font or a cured form, as described in 2012/0192880 to Dube et al., which is incorporated by reference herein. The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. In some embodiments, harvested tobacco can be sprayed with a buffer or antioxidant (e.g., a sodium metabisulfite buffer) to prevent the green plants from browning prior to further treatment as described herein. Other exemplary processing techniques are described, for example, in US Pat. Appl. Pub. Nos. 2009/0025739 to Brinkley et al. and 2011/0174323 to Coleman, III et al., which are incorporated by reference herein. At least a portion of the plant of the *Nicotiana* species can be treated with enzymes and/or probiotics before or after harvest, as discussed in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference.

In particular embodiments, the proteins of the protein-enriched materials to be treated (as well as the proteins comprising the resulting concentrates and isolates described herein) can comprise Fraction 1 ("F1") proteins and/or Fraction 2 ("F2") proteins. F1 proteins and F2 proteins generally make up the water-soluble protein portion of plant biomass. The F1 protein is an enzyme, known as ribulose-1,5-bisphosphate carboxylase-oxygenase (commonly referred to as RuBisCO), whose subunit molecular weight is about 550 kD. RuBisCO is largely considered to be the most abundant protein in the world, as it is present in every plant that undergoes photosynthesis. RuBisCO may comprise up to about 25% of the total protein content of a leaf and up to about 10% of the solid matter of a leaf RuBisCO is essential to the initial step of the photosynthetic fixation of carbon dioxide and functions to catalyze the carboxylation and/or oxygenation of ribulose-1, 5-bisphosphate. The F2 protein is a mixture of soluble proteins of cytoplasmic and chloroplastic origin. The proteins and peptides of the F2 protein generally have molecular weights ranging from about 3 kD to about 100 kD.

In certain embodiments, the protein-enriched materials treated according to the methods described herein are prepared according to the methods described in U.S. patent application Ser. No. 13/830,063 to Mua et al., filed Mar. 14, 2013, which is incorporated herein by reference, the subject matter of which is outlined briefly herein. According to the disclosure of U.S. patent application Ser. No. 13/830,063, one exemplary set of processing steps that can be carried out to obtain a RuBisCO-enriched extract and/or a F2 protein-enriched extract from a tobacco plant or portion thereof can include the following steps. A tobacco material can be homogenized to provide a solid pulp and a liquid, protein-containing extract. The extract can be clarified to remove solids therefrom, giving a solids fraction and a clarified, protein-containing extract. The extract is then pH-adjusted and separated into a liquid component and a solid, protein-containing precipitate. The precipitate generally comprises RuBisCO as well as various additional components. It is noted that the content of the precipitate may depend, in part, on the pH used in the previous step. For example, where the pH is between about 4.5 and about 6, the precipitate may comprise more RuBisCO, whereas where the pH is less than about 4.5, the precipitate may additionally include a significant amount of F2 proteins. The precipitate is subjected to filtration to give a protein-enriched material. Where a significant amount of F2 fraction is contained in the liquid component, that liquid component can be treated, for example, by filtration (e.g., through a filter or membrane on which the F2 proteins are generally retained, while allowing certain remaining components to pass through) or by precipitation (e.g., by adjusting the pH of the liquid component to a pH sufficient to precipitate the F2 proteins, such as less than about 4.5, preferably between about 3 and about 4.5).

An alternative exemplary process disclosed in U.S. patent application Ser. No. 13/830,063 for the production of a RuBisCO- and F2 protein-enriched material, RuBisCO-enriched material, and/or F2 protein-enriched material comprises the following steps. A tobacco material can be homogenized to provide a solid pulp and a liquid, protein-containing extract. The extract can then be clarified to remove solids therefrom (e.g., via a pH-adjustment step to provide an acidic or basic clarified, protein-containing extract), giving a solids fraction and a clarified, protein-containing extract. The extract is filtered and washed to give a solid, RuBisCO-enriched material, and a permeate. In certain embodiments, the permeate may comprise F2 proteins and the permeate can optionally be processed to give an F2 protein-enriched material.

Of course, it is to be understood that various additional processes can be used within these exemplary methods or in addition to the steps of the methods in the references cited herein and the methods described above. For example, typical separation processes can include one or more process steps such as solvent extraction (e.g., using polar solvents, organic solvents, or supercritical fluids), chromatography (e.g., preparative liquid chromatography), clarification, distillation, filtration (e.g., ultrafiltration), recrystallization, and/or solvent-solvent partitioning. In some embodiments, the tobacco plant or portion thereof can be pre-treated, e.g., to liberate certain compounds to make the desired compounds available for more efficient separation. In some embodiments, multiple methods are used to obtain the desired compounds.

Other exemplary means for extraction of proteins from tobacco and other plants include, but are not limited to, those described in U.S. Pat. No. 7,337,782 to Thompson; U.S. Pat. No. 6,033,895 to Garger et al.; U.S. Pat. No. 4,941,484 to Clapp et al.; U.S. Pat. Nos. 4,588,691 and 4,400,471 to Johal; U.S. Pat. No. 4,347,324 to Kwanyuen et al., U.S. Pat. No. 4,340,676 to Bourque; U.S. Pat. No. 4,333,871 to DeJong; U.S. Pat. Nos. 4,289,147 and 4,268,632 to Wildman et al.; U.S. Pat. Nos. 3,959,246, 3,823,128, and 3,684,520 to Bickoff et al.; US Pat. Appl. Publ. Nos. 2010/0093054 to Lo et al. and 2013/0072661 to Kale; U.S. patent application Ser. No. 13/830,063 to Mua et al., filed Mar. 14, 2013; Int'l Appl. Publ. Nos. WO2011/078671 to Van de Velde et al. and WO2008/143914 to Lo; and EP Pat. Publ. Nos. EP 2403888 to Parker et al.; EP 1691759 to Boddupalli et al.; and EP 1067946 to Brinkhaus et al., which are all incorporated by reference herein in their entireties. Other exemplary processing methods are provided, for example, in US Pat. Appl. Publ. No. 2012/0141648 to Morton et al., which is incorporated herein by reference.

A protein-enriched material used as a starting point in the purification processes discussed herein can be provided in varying forms. In some embodiments, the protein-enriched material is provided in a moistened form. In some embodiments, the protein-enriched extract is subjected to a solvent removal process such that the extract achieves a predominantly solid form. The protein-enriched extracts may be provided in a low solvent form. By the term "low solvent form" is meant that the solvent content including the moisture content of the material (e.g., a protein-enriched tobacco extract) is less than about 12 percent, based on the total weight of the material. Convenient methods for providing the protein-enriched extract in low solvent form include spray drying, freeze drying, belt drying, flash drying, or other such methods. It is particularly desirable to concentrate the liquid extract prior to spray drying or freeze drying the extract. A representative spray drying process is described in U.S. Pat. No. 3,398,754 to Tughan, which is incorporated herein by reference. A representative freeze drying process is described in U.S. Pat. No. 3,316,919 to Green, which is incorporated herein by reference. Methods and conditions for providing extracted materials in a low solvent or solid form (e.g., as a powder) will be apparent to the skilled artisan.

The protein-enriched material (e.g., extract) typically comprises some percentage of undesirable components and/or features. For example, in some embodiments, the protein-enriched material comprises an undesirable level or type of odor, taste, and/or color. In some embodiments, the protein-enriched material comprises an undesirable level of ash, an undesirable level of alkaloids (e.g., nicotine), and/or an undesirable level of heavy metals. According to the present disclosure, a crude protein-containing material (which may, in some embodiments, comprise RuBisCO and/or F2 proteins) isolated from a plant material is further treated to provide a protein composition (e.g., in the form of a concentrate or isolate) having a lower concentration of one or more of these undesirable components than prior to treatment. Various types of treatments are described herein, and it is to be understood that these treatments can be used independently or in combination. For example, one, some, or all of the treatments described herein may be used to further purify a crude, protein-containing material.

In certain embodiments, a protein-enriched material as described herein is treated to remove ash and/or alkaloids (e.g., nicotine). Ash is generally understood to be a solid, powdery substance remaining when water and organic matter is removed from a biomass sample and can include, for example, inorganic salts and minerals. Certain methods of preparing protein-enriched materials may generate some degree of ash, which can, in some embodiments, be retained in the protein-enriched material thus provided. For example, in some embodiments, the protein-enriched material can comprise as much as at least about 5% ash on a dry weight basis, at least about 10% ash on a dry weight basis, at least about 15% ash on a dry weight basis, or at least about 18% ash on a dry weight basis.

The ash removal treatment can, in some embodiments, comprise a diafiltration process. Diafiltration is a technique that uses ultrafiltration membranes to remove, replace, or lower the concentration of salts or solvents from solutions containing proteins, peptides, nucleic acids, and other biomolecules. The process employs permeable (porous) membrane filters to separate the components of solutions and suspensions based on their molecular sizes. An ultrafiltration membrane retains molecules that are larger than the pores of the membrane while smaller molecules such as salts, solvents and water, which are 100% permeable, freely pass through the membrane.

According to the present disclosure, diafiltration processes are advantageously selected which allow inorganic salts and/or nicotine to permeate the ultrafiltration membrane, while the protein is expected to remain in the retentate as it is much greater in molecular weight. In specific embodiments, a diafiltration process in which a 5 kDa molecular weight cut off (MWCO) filter membrane is capable of reducing (e.g., significantly reducing) the inorganic salt (ash) and/or nicotine content of a protein-enriched material. It is understood that various other MWCO filter membranes may provide similar results, provided that the molecular weight of the targeted protein or proteins are above the MWCO of the filter membrane and the molecular weights of the targeted compounds for removal (e.g., inorganic salts and/or nicotine) are well below the MWCO of the filter membrane.

As a general rule, it is understood that the MWCO of a membrane should be less than ⅓ times (e.g., between about ⅓ and about ⅙ times) the molecular weight of the molecule to be retained to ensure complete retention. The closer the MWCO of the filter membrane is to the molecular weight of the protein to be retained, the greater the possibility of some product loss during the filtration. For example, where the desired protein to be provided in the protein concentrate or isolate is RuBisCO, based on the known molecular weight of RuBisCO (490 kDa), it is understood that, e.g., filter membranes with MWCO values of 5 kDa, 10 kDa, 25 kDa, 50 kDa, 75 kDa, 100 kDa, or 150 kDa may provide sufficient removal of inorganic salts and/or nicotine and sufficient retention of protein. Such a process can advantageously be employed at both lab scale and at process scale successfully.

The solution for the diafiltration is generally water, although various other additives can be included. The diafiltration can, in some embodiments, be pH-controlled. For example, the diafiltration may be run in basic conditions in some embodiments; accordingly, a base (e.g., NaOH) can be added to ensure the desired pH of the solution undergoing the diafiltration process.

The diafiltration process can result in a reduction in ash (e.g., inorganic salts) and/or nicotine. For example, in some embodiments, the ash content can be reduced by at least about 25%, at least about 50%, at least about 75%, at least about 90%, at least about 95%, at least about 99%, at least about 99.9%, at least about 99.99%, or 100%. The final ash content in the protein concentrate or isolate thus provided is advantageously in certain embodiments less than about 15%, less than about 12%, less than about 10%, less than about 8%, less than about 5%, less than about 3%, less than about 2%, or less than about 1% (e.g., about 0%) by weight on a dry weight basis. In some embodiments, the nicotine content can be reduced by at least about 50%, at least about 75%, at least about 90%, at least about 95%, at least about 99%, at least about 99.5%, at least about 99.9%, or 100%. The final nicotine content in the protein concentrate or isolate thus provided is advantageously in certain embodiments less than about 10 µg/g, less than about 5 µg/g, less than about 1 µg/g, less than about 0.1 µg/g, less than about 0.01 µg/g (e.g., about 0 µg/g, or undetectable).

In further embodiments, a protein-enriched material as described herein is treated to remove one or more heavy metals. Heavy metals are metallic elements that are typically considered toxic and which have relatively high atomic weights, atomic numbers, and densities (typically having a specific gravity over 5.0). Exemplary heavy metals include cadmium, copper, lead, mercury, nickel, and the like. Various resins are, in certain embodiments, employed for the removal of such metals from protein-enriched materials according to the present disclosure. For example, in some embodiments, selective ion exchange resins (e.g., strong acid or weak acid cation resins), chelating resins, or activated carbon can be employed. Such resins may comprise various chelating groups (e.g., iminodiacetate, imidazole, triaminetetraacetic acid, and/or triaminetetraacetic acetate salt).

A wide range of resins are commercially available for removal of heavy metals from samples, and can be employed according to the present disclosure. Representative resins include, but are not limited to, Lewatit® TP resins, from Lenntech Water Treatment and Air Purification, Rotterdamseweg, The Netherlands; Purolite® Resins, from Purolite, Bala Cynwyd, Pa.; Dowex™ MAC-3, Marathon™, 21K, or M-43 resins, from The Dow Chemical Company, Midland, Mich.; CR20 resin or PK228L resin, from ITOCHU Chemicals America Inc., White Plains N.Y.; SiliaMetS® Imidazole Resin, SiliaMetS® TAAcOH Resin, or SiliaMetS® TAAcONa Resin, from Silicycle, Quebec, Canada, and combinations thereof.

In practice, the protein-enriched material can be treated with a resin for the removal of heavy metals in various ways. For example, the protein-enriched material can be dissolved, e.g., in water, and passed through a column/cartridge packed with the appropriate resin. In other embodiments, the protein-enriched material can be dissolved, e.g., in water, and the appropriate resin (in bulk form) can be added to the solution. In such embodiments, the resin-containing mixture can optionally be stirred and/or shaken to enhance the contact of the protein in the solution with the resin.

The solvent in which the protein-enriched extract is dissolved can be any solvent sufficient to dissolve the protein. In certain embodiments, the solvent is water, but various other solvents can be used independently or in combination with water. It may be preferable to control the pH of the solution, e.g., via the addition of an acid, base, or buffer. In some embodiments, the composition of the selected resin may dictate a certain operable pH range and the solution should be adjusted accordingly.

In certain embodiments, it may be beneficial to heat the resin and/or protein solution (e.g., by heating the column/ cartridge or by heating the resin mixture). The temperature at which the material is heated can vary and may, in some embodiments, be dependent upon the features of the specific resin chosen. In certain embodiments, the material can be heated between about room temperature and about 100° C. or between about room temperature and about 80° C. (e.g., between about 50° C. and about 70° C., such as at about 60° C.).

The time for which the protein-enriched material is in contact with the resin can also vary. For example, in some embodiments, 1 hour or less may be sufficient to provide adequate removal of undesirable metals. In other embodiments, it may be beneficial for the protein-enriched material to be in contact with the resin for a longer period of time (e.g., at least about 1 hour, at least about 2 hours, at least about 3 hours, at least about 4 hours, at least about 5 hours, or at least about 6 hours, such as between about 0.5 and 10 hours, between about 1 and about 8 hours, or between about 2 and about 7 hours).

In certain embodiments, a significant reduction in the metals content can be achieved using a combination of the Silicyle resins TAAcOH (a silica gel resin functionalized with triaminetetraacetic acid groups) and TAAcONa (a silica gel resin functionalized with triaminetetraacetate, sodium salt) in combination with heating and/or stirring. Specifically, this treatment, in certain embodiments, can reduce the content of copper, cadmium, lead, and nickel (individually) of the protein-enriched material by at least about 50%.

The overall reduction in heavy metal content following treatment with a resin can vary. Advantageously, in certain embodiments, treatment of a protein-enriched material as described herein can provide for a decrease in metals including copper, cadmium, lead, and nickel. For example, in some embodiments, resin treatment can provide a reduction of at least about 25%, at least about 50%, or at least about 75% of each of copper, cadmium, lead, and nickel as compared with an untreated sample prior to resin treatment.

The total heavy metal concentration in the protein concentrate or isolate provided by the invention is advantageously, in certain embodiments, less than about 60 μg/g, less than about 50 μg/g, less than about 40 μg/g, less than about 30 μg/g, less than about 20 μg/g, or less than about 10 μg/g. The combined concentration of cadmium, copper, lead, and nickel in the protein concentrate or isolate provided by the invention can be, in certain embodiments, less than about 40 μg/g, less than about 35 μg/g, less than about 30 μg/g, less than about 25 μg/g, less than about 20 μg/g, less than about 15 μg/g, less than about 10 μg/g, or less than about 5 μg/g.

In some embodiments, a protein-enriched material is processed via supercritical extraction. As used herein, the term "supercritical" means at or above the critical point of the solvent with respect to temperature and pressure. Supercritical extraction is a process by which an extractant is separated from a matrix, using a supercritical solvent as the extracting solvent. Supercritical extraction methods generally are taught, for example, in U.S. Pat. No. 5,435,325 to Clapp et al. and U.S. Pat. No. 7,638,155 to Irwin et al., which are incorporated herein by reference. In certain embodiments, the protein-enriched extract is treated prior to supercritical extraction by moistening (e.g., with water). For example, in certain embodiments, the protein-enriched extract is provided in a moistened form, having between about 5% and about 50% moisture by weight (e.g., between about 10% and about 50% moisture by weight).

The solvent used for the supercritical extraction can vary, and is any solvent suitable for supercritically extracting components from the protein-enriched extract. In particular, the solvent is capable of being provided in a supercritical state, extracting at least a portion of the components of the protein-enriched extract, and ultimately providing a further purified extracted protein isolate. Examples of solvents include carbon dioxide, n-propane, n-pentane, n-heptane, cyclohexane, n-hexanol, ethanol, n-pentanol, toluene, acetone, methyl acetate, diethylether, petroleum ethers, halogenated hydrocarbons such as dichloromethane and difluoroethane, and the like, as well as mixtures thereof.

The supercritical extraction solvent can optionally be employed along with predetermined amounts of modifiers (e.g., entrainers) that can, in some embodiments, serve to enhance solubility of the desired extraction targets in the supercritical solvent. Exemplary entrainers include hydrocarbons such as ethane, ethylene, propane, propylene, and the like. Such entrainers can be mixed with the supercritical solvent for the supercritical extraction step, or such entrainers can be mixed with the protein-enriched tobacco extract prior to the supercritical extraction. Various other modifiers (e.g., co-solvents) can be added to alter the extraction. For example, in certain embodiments, an organic co-solvent is added to the supercritical extraction solvent. The organic solvent can be, for example, ethanol, 1-butanol, isopropanol, methanol, 1-propanol, and mixtures thereof. The amount of entrainer or other modifier added to the supercritical extraction solvent can vary and may be, for example, between about 0% and about 50% by volume (e.g., between about 10% and about 30% by volume).

The amount of protein-enriched extract which is contacted with the supercritical solvent can vary. Typically, the weight of the solvent relative to the aqueously extracted tobacco components is great enough to provide efficient extraction of a significant amount of supercritically extracted components of the protein-enriched tobacco extract. The amount of solvent relative to the protein-enriched extract depends upon factors such as type of solvent, the temperature and pressure at which the supercritical extraction is performed, the type of tobacco which is being processed, the manner in which contact of the protein-enriched tobacco extract and supercritical solvent is conducted, and other such factors.

The conditions under which the supercritical extraction is performed can vary. Typical temperatures are above the critical temperature of the particular solvent. For example, in particular embodiments, the temperature of the supercritical extraction is up to about 70° C. (e.g., between about 0° C. and about 70° C.). For example, where the supercritical extraction solvent comprises $CO_2$, the extraction is generally performed between about 30° C. and about 70° C. (e.g., about 30° C. or about 60° C.). The pressure of the supercritical extraction may also vary. Exemplary pressure ranges are from about 0 mPa to about 35 mPa (e.g., about 10 mPa, about 20 mPa, or about 30 mPa). The solvent/tobacco mixture can be agitated or otherwise manipulated (e.g., stirred) in order to increase the rate at which extraction occurs. For example, conditions can be provided so as to provide good diffusion of the supercritical solvent within the protein-enriched extract or within the protein-enriched extract. Advantageously, the conditions are selected so as to avoid undesirable denaturation of the proteins.

Following the supercritical extraction, the resulting extracted material can be dried (e.g., by air drying) to provide a more purified protein composition. The protein composition can, in some embodiments, comprise a higher content of protein than the protein-enriched extract prior to supercritical extraction. For example, in some embodiments, the supercritical extraction described herein can provide at least about a 5%, 10%, 15%, 20%, or 25% increase in protein content by weight. Accordingly, the protein composition following supercritical extraction generally comprises at least about 50%, at least about 60%, at least about 70%, at least about 80%, at least about 90%, at least about 95%, at least about 98%, or at least about 99% protein (e.g., RuBisCO and/or F2 proteins) by dry weight.

Advantageously, in certain embodiments, the protein composition thus provided can exhibit a reduced nicotine content as compared with the protein-enriched extract. For example, in certain embodiments, the supercritical extraction can reduce the nicotine content by at least about 20%, at least about 30%, at least about 40%, at least about 50%, at least about 60%, at least about 70%, at least about 80% relative to the protein-enriched extract (prior to supercritical extraction). For example, in some embodiments, the supercritical extraction can reduce the nicotine content by between about 5% and about 100%, e.g., between about 20% and about 100%, or between about 50% and about 100%) relative to the protein-enriched extract (prior to supercritical extraction).

In some embodiments, the supercritical extraction unexpectedly alters various other features of the protein-enriched extract subjected to the extraction. For example, in some embodiments, the protein-enriched extract can exhibit an off-taste (e.g., a salty or otherwise negative taste), which can be significantly reduced or muted by the supercritical extraction process. Similarly, in some embodiments, the protein-enriched extract can exhibit an off-odor (e.g., an earthy odor), which can be significantly reduced or removed by the supercritical extraction process. Further, the protein-enriched extract can exhibit a color (e.g., yellowish, brownish) that can be significantly reduced or removed by the supercritical extraction process. The improvement in odor, taste, and/or color of the supercritically extracted concentrate or isolate over the untreated extract can be quantified by any known method. For example, a sensory panel can be used to evaluate the change in odor and or taste, whereas optical methods (e.g., light absorption) can be used to evaluate the change in color. Accordingly, in certain embodiments, a tasteless, colorless, and/or odorless protein concentrate or isolate is provided according to the methods described herein.

The form of the protein composition provided according to the present invention (e.g., a RuBisCO concentrate or isolate, combined RuBisCO/F2 protein concentrate or isolate, and/or F2 concentrate or isolate) obtained according to the methods of the present disclosure can vary. Typically, these materials are in solid, liquid, or semi-solid or gel forms. The resulting formulations can be used in concrete, absolute, or neat form. Solid forms of the concentrates or isolates described herein can include spray-dried and freeze-dried forms. Liquid forms of the concentrates or isolates described herein can include formulations contained within aqueous or organic solvent carriers.

The methods disclosed herein may, in some embodiments, provide a protein concentrate or isolate comprising at least about 50%, at least about 60%, at least about 70%, at least about 80%, or at least about 90% protein by dry weight. In some embodiments, the protein concentrate or isolate comprises a mixture of RuBisCO and F2 proteins. In some embodiments, the protein in the protein concentrate or isolate comprises primarily RuBisCO. In some embodiments, the protein in the protein concentrate or isolate comprises primarily F2 proteins.

In some embodiments, the protein concentrate or isolate comprises at least about 50%, at least about 60%, at least about 70%, at least about 80%, or at least about 90% F1 protein by weight. In some embodiments, the present disclosure specifically provides a method for the isolation and/or purification of RuBisCO extracted from a plant of the Nicotiana species or a portion thereof. Accordingly, the methods disclosed herein may, in some embodiments, provide a RuBisCO concentrate or isolate, e.g., a material comprising at least about 50%, at least about 60%, at least about 70%, at least about 80%, or at least about 90% RuBisCO by dry weight.

In some embodiments, the protein concentrate or isolate comprises at least about 50%, at least about 60%, at least about 70%, at least about 80%, or at least about 90% F2 protein by dry weight.

Although in some embodiments, the protein concentrate or isolate described herein can be used directly following the one or more treatment steps, it may be desirable to thermally treat the material in order to, for example, pasteurize the material or otherwise chemically alter the material. See, for example, US Pat. Pub. No. 2010/0300463 to Chen et al., which is incorporated herein by reference. In some embodiments, in addition to or in place of the optional heat treatment, tobacco material can be irradiated (e.g., to ensure no microbes are associated with the protein concentrate or isolate).

In some embodiments, the methods described herein can be used in combination with other types of treatment processes, which may, for example, further purify or modify the concentrate or isolate. For example, in some embodiments, the protein-enriched composition is brought into contact with an imprinted polymer or non-imprinted polymer such as described, for example, in US Pat. Pub. Nos. 2007/0186940 to Bhattacharyya et al; 2011/0041859 to Rees et al.; and 2011/0159160 to Jonsson et al; and U.S. patent application Ser. No. 13/111,330 to Byrd et al., filed May 19, 2011, all of which are incorporated herein by reference. Treatment with a molecularly imprinted or non-imprinted polymer can be used to remove certain components of the protein-enriched composition. In some embodiments, the protein-enriched composition described herein can be subjected to conditions so as to cause compounds contained in such material to undergo chemical transformation and/or degradation. Exemplary chemical transformation techniques are set forth in US Pat. Appl. Pub. Nos. 2011/0174323 to Coleman, III, et al. and 2011/0259353 to Coleman, III et al., which are incorporated by reference herein.

The protein concentrates and isolates (i.e., RuBisCO concentrates and isolates, combined RuBisCO/F2 protein concentrates and isolates, and/or F2 protein concentrates and isolates) provided following any one or more of the purification treatment processes described herein can advantageously be used in various applications. For many applications (e.g., food products, feed products, and industrial products), it may be desirable to replace certain animal proteins with plant proteins. Additionally, in some applications, it may be desirable to replace certain other plant proteins typically used (e.g., soy proteins and/or genetically modified proteins). Protein concentrates and isolates such as those provided by the methods described herein can exhibit good nutritional properties and, in some embodiments, can be provided in a form that has a reduced content of various undesirable components (e.g., ash, metal salts, alkaloids (e.g., nicotine), heavy metals, and other impurities/contaminants) and/or modified sensory characteristics (e.g., odor, taste, and/or color), making them particularly suitable for use in various products. Further, certain physical properties of RuBisCO render it advantageous for use in such products, as it has excellent binding, gelling, solubility, and emulsifying behavior. In some embodiments, the types of treatment described herein may provide a food-grade protein-containing material. In certain embodiments, the protein concentrate isolate comprises a protein material that exceeds soy protein in nutritional quality. In some embodiments, the protein concentrate or isolate may be useful for medicinal purposes.

Processed materials that are provided in accordance with the present invention are useful ingredients for a wide variety of commercial applications. The materials can be used as binders, fillers or extenders, or can serve other functions or impart functional attributes, in a wide variety of industrial formulations. For example, the materials can be used as components of various types of resins that have industrial applications; and additionally can be used as components of coatings (e.g., for inks and paints) and of adhesives (e.g., for glues and hot melt formulations). The materials can be used as components of a wide variety of cosmetic formulations (e.g., the materials can be incorporated within shampoos and skin care products). The materials can be used as components of foods, dietary supplements and functional foods (e.g., as components of beverages, processed food products, and the like). The materials also can be used components of animal feed. The materials can be used as components of pharmaceutical formulations (e.g., as components of liquids, gums, lozenges, tablets and pills that are used for medicinal purposes). Additionally, the materials can be used as components of tobacco products; such as components of tobacco burning products (e.g., cigarettes, cigars, pipe tobaccos, and the like), tobacco heating smoking articles (e.g., cigarettes such as those sold under the brand name Eclipse by R. J. Reynolds Tobacco Company), smokeless tobacco products (e.g, moist snuff, chewing tobacco, snus and so-called dissolvable tobacco products), so-called electronic cigarettes, and the like.

With regard to use in tobacco burning products, the concentrates and isolates described herein can be used in various capacities. For example, in certain embodiments, the concentrates and isolates can be mixed with casing materials and applied to tobacco as a casing ingredient or as a top dressing, incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in US Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Referring to FIG. 1, there is shown a smoking article 10 in the form of a cigarette and possessing certain representative components of a smoking article that can contain the protein composition of the present invention. The cigarette 10 includes a generally cylindrical rod 12 of a charge or roll of smokable filler material (e.g., about 0.3 to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The protein composition of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

With regard to use of the disclosed protein compositions in aerosol-generating devices that contain nicotine and/or tobacco material (or some portion or component thereof) that is not intended to be combusted during use, including so-called "e-cigarettes," exemplary details are provided, for example, in US Pat. Pub. No. 2012/0192880 to Dube et al., which is incorporated by reference herein. See, for example, the various alternative smoking articles, aerosol delivery devices and heat generating sources set forth in the background art described in U.S. Pat. No. 7,726,320 to Robinson et al., U.S. patent application Ser. No. 13/432,406, to Griffith, Jr. et al., filed Mar. 28, 2012, U.S. patent application Ser. No. 13/536,438, to Sebastian et al., filed Jun. 28, 2012, U.S. patent application Ser. No. 13/602,871, to Collett et al., filed Sep. 4, 2012, U.S. patent application Ser. No. 13/647,000, to Sears et al., filed Oct. 8, 2012, and U.S. patent application Ser. No. 13/840,264, to Novak, III et al., filed Mar. 15, 2013, which are incorporated herein by reference.

With regard to use of the disclosed concentrates and isolates in smokeless tobacco products, exemplary products include loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. Various types of smokeless tobacco products are described or referenced in US Pat. Pub. No 2012/0152265 to Dube et al., which is incorporated herein by reference. Further ingredients can be admixed with, or otherwise incorporated within, smokeless tobacco compositions according to the invention. Exemplary encapsulated additives are described, for example, in WO 2010/132444 to Atchley, which has been previously incorporated by reference herein. See also, the smokeless tobacco ingredients set forth in US Pat. Pub. Nos. 2012/0055494 to Hunt et al. and 2012/0199145 to Byrd et al., which are incorporated by reference herein.

Figure 2:
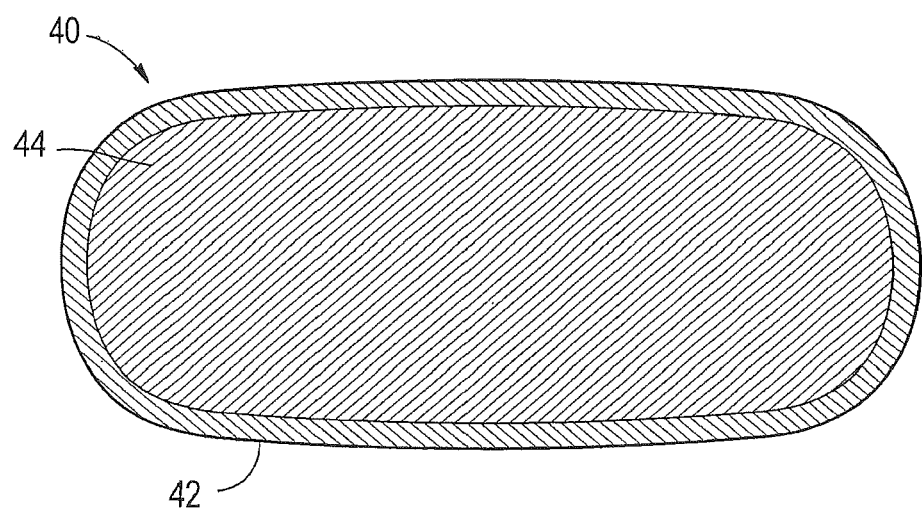
FIG. 2 is a cross-sectional view of a smokeless tobacco product embodiment, taken across the width of the product, showing an outer pouch filled with a smokeless tobacco composition of the invention.

Referring to FIG. 2, a representative snus type of tobacco product comprising a concentrate or isolate of the present invention is shown. In particular, FIG. 4 illustrates a smokeless tobacco product 40 having a water-permeable outer pouch 42 containing a smokeless tobacco composition 44. Any of the components of the tobacco product can comprise a tobacco-derived protein material as described herein (e.g., the interior or exterior of the pouch lining or a portion of the smokeless tobacco composition contained therein).

The amount of protein concentrate or isolate of the present invention incorporated within a tobacco composition or tobacco product can depend on the desired function of the concentrate or isolate, the chemical makeup of the concentrate or isolate, and the type of tobacco composition to which the concentrate or isolate is added. The amount of concentrate or isolate added to a tobacco composition can vary, but will typically not exceed about 50 weight percent based on the total dry weight of the tobacco composition to which the concentrate or isolate is added. For example, the amount of concentrate or isolate added to a tobacco composition may be in the range of about 0.25 to about 25 weight percent or about 1 to about 10 weight percent, based on the total dry weight of the tobacco composition.

Although the use of such protein concentrates and isolates is generally described in the context of tobacco compositions, it is noted that such formulations can be applicable in many other types of compositions, e.g., in dietary supplements as described in U.S. patent application Ser. No. 13/830,063 to Mua et al., filed Mar. 14, 2013, which is incorporated herein by reference.

EXPERIMENTAL

Aspects of the present invention is more fully illustrated by the following examples, which are set forth to illustrate certain aspects of the present invention and are not to be construed as limiting thereof.

Example 1

Exemplary Provision of RuBisCO-Enriched Extract by Acidic Clarification and Precipitation Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.6. This protein-containing extract is clarified first by passing the extract through a decanter. The pH of the protein-containing extract is adjusted to 5.9 using hydrochloric acid. Diatomaceous earth is optionally added to the extract, the mixture is stirred for 15 minutes, and then passed through a filter press.

The resulting clarified, protein-containing extract is treated with citric acid and hydrochloric acid to adjust the pH to 4.92. The pH-adjusted extract is left to sit for 47 hours. Liquid is decanted from the top of the mixture and a settled solid at the bottom of the mixture is obtained and processed on a 1.4 μm ceramic filter using tangential flow filtration. The retentate therefrom is concentrated to give a protein-enriched tobacco-derived material. The materials thus obtained comprise between about 85 and about 99% protein by weight.

Example 2

Exemplary Provision of RuBisCO-Enriched Extract by Acidic Clarification

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.4. This protein-containing extract is clarified first by passing the extract through a decanter. The pH of the protein-containing extract is adjusted to 5.9 using hydrochloric acid. Diatomaceous earth is optionally added to the extract, the mixture is stirred for 15 minutes, and then passed through a filter press. The filtrate is washed with water, pH adjusted to 5.9 to increase recovery of protein.

The resulting clarified, protein-containing extract is processed on a 500 kDa reverse osmosis filter using tangential flow filtration. The retentate is washed with a glycine solution (75 mM glycine at pH 10.5) to give a RuBisCO-enriched tobacco-derived material retentate (comprising about 75-85% protein by weight). The permeate is cooled to 8° C. and processed on a 1 kDa reverse osmosis filter using tangential flow filtration. The 1 kDa retentate is washed with the glycine solution and concentrated to give a F2 protein-enriched tobacco-derived material (comprising about 30-40% F2 protein, although higher percentages, e.g., 65% have been obtained using alternate filtration methods, e.g., using 10 kDa and/or 20 kDa filters in place of the 1 kDa filter).

Example 3

Exemplary Provision of RuBisCO-Enriched Extract by Acidic Clarification and Precipitation Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.7. This protein-containing extract is clarified first by passing the extract through a decanter. The pH of the protein-containing extract is adjusted to 5.9 using hydrochloric acid. Diatomaceous earth is added to the extract, the mixture is stirred for 15 minutes, and then passed through a filter press.

The resulting clarified, protein-containing extract is treated with hydrochloric acid to adjust the pH to 4.98. The pH-adjusted extract is left to sit for 60 hours. Liquid is decanted from the top of the mixture and a settled solid at the bottom of the mixture is obtained and processed on a 1.4 μm ceramic filter using tangential flow filtration. The retentate therefrom is concentrated to give a protein-enriched tobacco-derived material. The materials thus obtained comprise between about 85 and about 99% protein by weight.

Example 4

Exemplary Provision of RuBisCO-Enriched and F2-Enriched Extracts by Basic Clarification Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.5. This protein-containing extract is clarified first by passing the extract through a decanter. The pH of the protein-containing extract is adjusted to 10.5 using sodium hydroxide. Activated carbon is added and diatomaceous earth is added to the extract, the mixture is stirred for 15 minutes, and then brought into contact with a filter press. As the mixture was not passing through the filter press, the pH of the mixture is adjusted to 5.9 using hydrochloric acid and then passes through the filter press.

The resulting clarified, protein-containing permeate is processed on a 500 kDa reverse osmosis filter using tangential flow filtration. The retentate is washed with a glycine solution (75 mM glycine at pH 10.5), giving a RuBisCO protein-containing retentate (comprising about 75-85% protein by weight) and stored. The permeate is cooled to 8° C. and processed on a 1 kDa reverse osmosis filter using tangential flow filtration. The retentate is washed with the glycine solution and concentrated to give a F2 fraction protein-enriched tobacco-derived material (comprising about 30-40% F2 protein, although higher percentages, e.g., 65% have been obtained using alternate filtration methods, e.g., using 10 kDa and/or 20 kDa filters in place of the 1 kDa filter).

Example 5

Exemplary Provision of RuBisCO-Enriched and F2-Enriched Extracts by Acidic Clarification and Precipitation Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.4. This protein-containing extract is clarified first by passing the extract through a decanter. The pH of the protein-containing extract is adjusted to 5.9 using hydrochloric acid. Activated carbon is added and diatomaceous earth is added to the extract, the mixture is stirred for 15 minutes, and then passed through a filter press. The resulting clarified, protein-containing permeate is processed on a 500 kDa reverse osmosis filter using tangential flow filtration. The retentate is washed with a glycine solution (75 mM glycine at pH 10.5), giving RuBisCO protein-containing retentate (comprising about 75-85% protein by weight), which is stored. The permeate is cooled to 8° C. and processed on a 1 kDa reverse osmosis filter using tangential flow filtration. The retentate is washed with the glycine solution and concentrated to give a F2 fraction protein-enriched tobacco-derived material (comprising about 30-40% F2 protein, although higher percentages, e.g., 65% have been obtained using alternate filtration methods, e.g., using 10 kDa and/or 20 kDa filters in place of the 1 kDa filter).

Example 6

Exemplary Provision and Separation of RuBisCO-Enriched and F2-Enriched Extracts

Tobacco plants are harvested, chipped, and homogenized in a disintegrator by adding water thereto and the material is then passed into a horizontal screw press for liquid extraction. The liquid protein-containing extract thus obtained is a green juice having a pH of 5.6. The pH of the protein-containing extract is adjusted to 7.10 using sodium hydroxide. Diatomaceous earth is added to the extract, the mixture is stirred for 15 minutes, and then passed through a filter press. The resulting clarified, protein-containing permeate is processed on a 1 kDa filter using tangential flow filtration. The retentate comprises a mixture of RuBisCO and F2 proteins and comprises approximately 50% protein.

Example 7

Diafiltration (Lab Scale)

A sample of protein-enriched extract prepared, e.g., according to any of Examples 1-6, above, is dissolved in water and the pH of the solution is adjusted to 9.5 by adding sodium hydroxide. The solution is introduced into a Koch Membrane Systems (KMS) Demofilter Unit equipped with a KMS Romicon Hollow Fiber 5 kDA MWCO filter with additional water. The solution is filtered on the system with the regular addition of water at approximate 20 min intervals to ensure constant volume of retentate. The pH of the retentate is kept at ~9.5-10 with periodic addition of NaOH and pH measurements after water additions. This pH was chosen so as to maintain the protein solubility, ensure free base nicotine permeability, and inorganic salt dissociation from the protein. The permeate is monitored qualitatively for color and also for pH. The permeate was initially yellow and became clear near the end of the diafiltration experiment. The retentate was concentrated to 10% dissolved solids at a final pH of 7-8 and freeze dried.

The diafiltration process provided recovery of 37 g of freeze dried product from the original 50 g of starting material, or 74% recovery and 26% mass loss. The protein-enriched extract contained 18.7% ash and 2830 µg/g nicotine, having a pH of 8.5. Following the diafiltration process, the product contained 9% ash and less than 1.0 µg/g nicotine, having a final pH of 7.5. The final protein concentration in the product was 90% on a dry weight basis (as compared with a protein concentration of 78% in the protein-enriched material prior to diafiltration).

Example 8

Diafiltration (Process Scale)

A sample of protein-enriched extract prepared, e.g., according to any of Examples 1-6, above, is dissolved in water and added to the reservoir of a Filtration Engineering Model 93 RO/UF unit equipped with (4) 3.8"×40" Snyder 5 kDa spiral wound ultrafiltration membranes. The unit is turned on in recirculation mode and NaOH is added to bring pH to 9.5 to ensure solubilization of the protein. The permeate valve is opened and water is added to the reservoir at the same flow rate as the permeate. The amount of water utilized for the diafiltration can be based on lab-scale diafiltration (e.g., Example 7). The permeate flow rate is 2 gal per minute and the total diafiltration time is 330 min (5.5 hr). The pH is monitored every 30 minutes and adjusted to 9.5 with NaOH. At the 4.5 hr mark, no additional pH adjustment is performed and, after 5.5 hours, the feed water is shut off and the retentate is concentrated to 10% dissolved solids. The final pH of the retentate was 7.8. The retentate was collected, stored at 4° C., and spray dried.

The diafiltration process provided recovery of about 5 lbs of spray dried product, due to various difficulties in processing, which can readily be addressed. Based on the results of the laboratory scale process (Example 7), it would be expected to result in an estimated 14.8 lbs of product from the 20 lbs. of starting material. The original protein-enriched extract contained 18.7% ash and 2830 μg/g nicotine, having a pH of 8.5. Following the diafiltration process, the product contained 5.5% ash and less than 1.0 μg/g nicotine, having a final pH of 8.1. The final protein concentration in the product was 93% on a dry weight basis (as compared with a protein concentration of 78% in the protein-enriched material prior to diafiltration).

Example 9

Heavy Metal Removal

Following diafiltration (e.g., as in Example 7 or 8), the protein isolate thus provided is treated with a resin (described in greater detail below). The protein concentrate is mixed with the resin and water and the resulting mixture is shaken for 1 hour. After 1 hour, the mixture is centrifuged. The supernatant is separated and tested for metals.

a) ITOCHU CR20 Resin

The first resin is a chelating resin with polyamine functionality (CR20 resin, from ITOCHU Chemicals America Inc., White Plains N.Y.). Treatment with this resin provided no change in the total content of cadmium, copper, lead, or nickel.

b) ITOCHU PK228L Resin

The second tested resin has a porous styrene DVB polymer matrix with sulfonic acid groups (PK228L resin, from ITOCHU Chemicals America Inc., White Plains N.Y.). Treatment with this resin provided no change in the total content of cadmium, copper, lead, or nickel.

c) Silicycle SiliaMetS® Imidazole Resin

The third tested resin is a silica gel resin functionalized with imidazole groups (SiliaMetS® Imidazole Resin, from Silicycle, Quebec, Canada). Two different variants of this resin were used (an Imidazole 200 mg resin and an Imidazole 500 mg resin). Treatment with this resin provided no change in the total content of cadmium, copper, lead, or nickel.

d) Silicycle SiliaMetS® TAAcOH and TAAcONa Resins

The fourth tested resin is a combination (equal amounts) of two resins: 1) a silica gel resin functionalized with triaminetetraacetic acid (TAAcOH) groups (SiliaMetS® TAAcOH Resin, from Silicycle, Quebec, Canada), and 2) a silica gel resin functionalized with triaminetetraacetate, sodium salt (TAAcONa) groups (SiliaMetS® TAAcONa Resin, from Silicycle, Quebec, Canada). According to the manufacturer, higher scavenging rates can sometimes be achieved at higher shake times and/or increased temperature; therefore, these parameters were modified to evaluate the effect of each.

One protein concentrate sample was treated as described above; one protein concentrate sample was shaken with the TAAcOH/TAAcONa resins for 3 hours rather than 1 hour; one protein concentrate sample was shaken with the TAAcOH/TAAcONa resins for 6 hours rather than 1 hour; one protein concentrate sample was not shaken and was instead heated at 60° C. for 3 hours with the TAAcOH/TAAcONa resins; one protein concentrate sample was not shaken and was instead heated at 60° C. for 6 hours with the TAAcOH/TAAcONa resins; and one protein concentrate sample was shaken with double the amount of TAAcOH/TAAcONa resins for 1 hour.

The greatest reduction in metal content was achieved with the TAAcOH/TAAcONa resins by heating the mixture at 60° C. or with the TAAcOH/TAAcONa by shaking the mixture for 3 hours. These treatments reduced the majority of the metals by greater than 50%. The results obtained for cadmium, copper, lead, and nickel are provided below in Table 1.

TABLE 1

| SiliaMetS TAAcOH and TAAcONa resin treatment (μg/g) | | | | |
|---|---|---|---|---|
| Sample | Cadmium | Copper | Lead | Nickel |
| Control | 12.7843 | 51.5648 | 0.4939 | 0.7811 |
| TAAcOH/TAAcONa shake | 8.2106 | 31.2078 | 0.0821 | 0.3797 |
| TAAcOH/TAAcONa heat | 6.2763 | * | 0.1168 | 0.4434 |

* below detection limits

Example 10

Supercritical Extraction

A sample of protein-enriched extract in spray-dried form is added to an extraction vessel and contacted with a solvent comprising supercritical carbon dioxide with 10% ethanol by volume. The extraction is conducted at a pressure of 10 mPa and a temperature of about 40° C. By comparing nicotine peak areas between a control sample of protein-enriched extract and the extracted material, it is determined that the nicotine was reduced by supercritical extraction by approximately 80%. The odor of the concentrate, before and after supercritical extraction, is informally evaluated and noted to be muted following the supercritical extraction.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method for reducing the ash or alkaloid content in a protein-enriched material, the method comprising:
   a) receiving a plant-derived, protein-enriched material comprising RuBisCO, F2 fraction proteins, or a combination thereof, wherein the plant-derived, protein-enriched material further comprises undesirable ash, nicotine, or a combination thereof;
   b) dissolving at least a portion of the plant-derived, protein-enriched material in a solvent to form a solution having a basic pH;
   c) subjecting the plant-derived, protein-enriched material solution to diafiltration by passing the solution through one or more ultrafiltration membranes to afford a retentate comprising a protein concentrate or isolate having a reduced amount of ash, nicotine, or a combination thereof as compared with the plant-derived, protein-enriched material.

2. The method of claim 1, wherein the solvent is aqueous.

3. The method of claim 1, wherein the plant-derived, protein-enriched material comprises material from a plant of the *Nicotiana* species.

4. The method of claim 1, wherein the one or more ultrafiltration membranes have a molecular weight cutoff of between about 1 kDa and about 150 kDa.

5. The method of claim 1, wherein the subjecting step comprising passing the solution through a ultrafiltration membrane having a molecular weight cutoff of about 5 kDa.

6. The method of claim 1, wherein the protein concentrate or isolate has an ash content that is reduced at least about 25% as compared with the plant-derived, protein-enriched material.

7. The method of claim 1, wherein the protein concentrate or isolate has an ash content of less than about 10% by weight.

8. The method of claim 1, wherein the protein concentrate or isolate has a nicotine content of less than about 5 µg/g.

9. The method of claim 1, wherein the plant-derived, protein-enriched material comprises at least about 40% RuBisCO, F2 fraction proteins, or a combination thereof.

10. The method of claim 1, wherein the protein concentrate or isolate has a nicotine content of less than about 1 µg/g.

11. The method of claim 1, further comprising
treating at least a portion of the plant-derived, protein-enriched material before step b) or the retentate following step c) by contacting it in solution with a functionalized resin to reduce the amount of one or more of copper, cadmium, lead, and nickel.

12. The method of claim 11, wherein the treating is conducted in an aqueous solution.

13. The method of claim 11, wherein the treating is conducted at a pH of greater than 7.

14. The method of claim 11, wherein the plant-derived, protein-enriched material comprises material from a plant of the *Nicotiana* species.

15. The method of claim 11, wherein the treating step comprises stirring the plant-derived, protein-enriched material or retentate with the functionalized resin.

16. The method of claim 11, wherein the contacting step comprises passing the plant-derived, protein-enriched material or retentate through a column comprising the functionalized resin.

17. The method of claim 11, wherein the functionalized resin comprises a resin functionalized with triaminetetraacetic acid groups or salts thereof.

18. The method of claim 11, wherein the treating is conducted at a temperature between about room temperature and about 80° C.

19. The method of claim 11, wherein the treating comprises agitating the plant-derived, protein-enriched material or retentate and the functionalized resin.

20. The method of claim 11, wherein the treating provides a material that has an amount of one or more of copper, cadmium, lead, and nickel that is reduced at least about 25% as compared with the plant-derived, protein-enriched material or retentate.

21. The method of claim 11, wherein the treating provides a material that has an amount of one or more of copper, cadmium, lead, and nickel that is reduced at least about 50% as compared with the plant-derived, protein-enriched material or retentate.

22. The method of claim 11, wherein the plant-derived, protein-enriched material comprises at least about 40% RuBisCO, F2 fraction proteins, or a combination thereof.

* * * * *